United States Patent [19]

Naggert et al.

[11] Patent Number: 5,593,837
[45] Date of Patent: Jan. 14, 1997

[54] CLINICAL DISORDERS ASSOCIATED WITH CARBOXYPEPTIDASE E MUTATION

[75] Inventors: Jürgen K. Naggert; Edward H. Leiter, both of Bar Harbor, Me.

[73] Assignee: The Jackson Laboratory, Bar Harbor, Me.

[21] Appl. No.: 452,262

[22] Filed: May 26, 1995

[51] Int. Cl.$^6$ .............................. C12G 1/68; C12N 9/48
[52] U.S. Cl. .................. 435/6; 435/212; 436/63; 436/811; 424/94.63
[58] Field of Search .................... 435/212, 6; 424/94.63; 436/811, 63

[56] References Cited

PUBLICATIONS

Fricker, Lloyd D., *Neuroprotocols* 5: 001 (1994).
Manser et al., *Biochem J.* 267: 517 (1990).
Castano et al. "Identification and cloning of a granule autoantigen (carboxypeptidase–H) associated with Type I diabetes" J. Clin. Endocrin. Metab. 73(6), 1197–1201. 1991.

*Primary Examiner*—Robert A. Wax
*Assistant Examiner*—Nashaat T. Nashed
*Attorney, Agent, or Firm*—Kevin M. Farrell

[57] ABSTRACT

Disclosed herein is a therapeutic method for treating a clinical disorder associated with a mutation in the carboxypeptidase E gene. In the therapeutic method of the invention, a molecule having carboxypeptidase activity is introduced into the plasma of the individual being treated. Such molecules include, for example, carboxypeptidase H, carboxypeptidase M, carboxypeptidase N, carboxypeptidase U and carboxypeptidase B. Also disclosed are methods for identifying individuals falling within the class for which the therapeutic method described above can be effective. These methods include, for example, the isolation of DNA encoding carboxypeptidase E followed by either: 1) sequence determination and comparison to wild-type; or 2) expression and comparison of activity to wild-type activity. Also disclosed are oligonucleotide probes useful for diagnosing a clinical disorder such as obesity, impaired glucose tolerance and diabetes in an individual, the clinical disorder being associated with a mutation in the carboxypeptidase E gene.

5 Claims, 5 Drawing Sheets

| | | | | | | | | | | | | | | |
|---|---|---|---|---|---|---|---|---|---|---|---|---|---|---|
| mouseCPE | M | D | I | P | F | V | L | S | A | N | L | H | G | G | D | (SEQ ID NO.13) |
| ratCPE | M | D | I | P | F | V | L | S | A | N | L | H | G | G | D | (SEQ ID NO.14) |
| humanCPE | M | D | I | P | F | V | L | S | A | N | L | H | G | G | D | (SEQ ID NO.15) |
| bovineCPE | M | D | I | P | F | V | L | S | A | N | L | H | G | G | D | (SEQ ID NO.16) |
| fishCPE | M | E | I | P | F | V | L | S | A | N | L | H | G | G | D | (SEQ ID NO.17) |
| flyCP? | L | S | L | P | F | V | L | S | A | N | L | H | G | G | S | (SEQ ID NO.18) |
| humanCPM | K | T | E | T | F | V | L | S | A | N | L | H | G | G | A | (SEQ ID NO.19) |

FIGURE 4

CLINICAL DISORDERS ASSOCIATED WITH CARBOXYPEPTIDASE E MUTATION

GOVERNMENT SUPPORT

Experimental work described herein was supported by grants from the United States Government which may have certain rights in the invention.

BACKGROUND OF THE INVENTION

Many clinical disorders are characterized as etiologically diverse, thereby complicating diagnosis and treatment. Diabetes mellitus, the most prevalent of the endocrine diseases, is one example. The disease, which is characterized by metabolic abnormalities and by long-term complications involving the eyes, kidneys, nerves and blood vessels, has been estimated to affect between 1–2% of the population.

The National Diabetes Data Group has defined two broad Categories: insulin-dependent diabetes and non-insulin-dependent diabetes. A therapeutic regimen including insulin therapy does not necessarily imply a disease classification of insulin-dependence. Rather, the term insulin-dependent is applied to that subcategory of diabetics at risk for ketoacidosis in the absence of insulin. Many of the patients who receive insulin therapy to control plasma glucose levels are not at risk for ketoacidosis if exogenous insulin is not administered.

A further classification which appears in the literature is the primary and secondary classification. The primary classification implies that no associated disease is present, while the secondary classification indicates some associated abnormality which causes or allows a diabetic syndrome to develop (e.g., pancreatic disease, hormonal abnormalities, drug or chemical induction, insulin receptor abnormalities, genetic disorders, etc.).

In light of the fact that a significant percentage of identical twins remain discordant for diabetes, an environmental factor (e.g., viral infection of beta cells) is believed to play a role in the development of many diabetic syndromes. It is possible, however, to identify genetic abnormalities as likely causes for diabetic syndromes. The ability to associate a specific etiology with a particular clinical disorder, such as a diabetic syndrome, is valuable to the clinician in formulating a therapeutic regimen.

SUMMARY OF THE INVENTION

The present invention relates, in one aspect, to a therapeutic method for treating a clinical disorder associated with a mutation in the carboxypeptidase E gene. In the therapeutic method of the invention, a molecule having carboxypeptidase activity is introduced into the plasma of the individual being treated. Among the clinical disorders to which the invention relates are obesity, diabetes or impaired glucose tolerance.

The molecule having carboxypeptidase activity is characterized by the ability to remove a diarginyl C-terminal extension from the insulin B-chain under physiological conditions. Such molecules include, for example, carboxypeptidase H, carboxypeptidase M, carboxypeptidase N, carboxypeptidase U and carboxypeptidase B.

Individuals falling within the class for which the therapeutic method described above can be effective are identified in a variety of ways. For example, DNA encoding carboxypeptidase E can be isolated from the individual. Using conventional recombinant DNA techniques, the isolated DNA can be expressed in cells. Following expression and lysis of the cells, the enzymatic activity of the expressed carboxypeptidase E can be determined, and compared with levels of activity determined for wild-type carboxypeptidase E which is produced and assayed in an otherwise identical manner. A substantial reduction in the enzymatic activity relative to that of wild-type is indicative of the clinical disorder (e.g., impaired-glucose tolerance, diabetes or obesity) associated with a mutation in the carboxypeptidase E gene.

A second method for identifying an individual afflicted with a clinical disorder associated with a mutation in the carboxypeptidase E gene involves the isolation of DNA which encodes carboxypeptidase E from the individual. The sequence of nucleotides is then determined by conventional techniques. The sequence of nucleotides is then compared with the nucleotide sequence of a gene encoding a wild-type form of carboxypeptidase E, a difference between the compared nucleotide sequences being indicative of a clinical disorder associated with a mutation in the carboxypeptidase E gene.

In another aspect, the invention relates to an oligonucleotide probe useful for diagnosing a clinical disorder such as obesity, impaired glucose tolerance and diabetes in an individual, the clinical disorder being associated with a mutation in the carboxypeptidase E gene. Such an oligonucleotide probe is characterized by the ability to hybridize specifically to a mutant allele of the carboxypeptidase E gene.

BRIEF DESCRIPTION OF THE DRAWINGS

FIG. 4 BKS-fat/fat mice, but not BKS or HRS mice, carry a T→C mutation in position 729, resulting in the incorporation of a Pro residue in position 202 of the carboxypeptidase E protein. Sequence alignment of CPE from five species around amino acid residue 202 is shown. This sequence segment is highly conserved in all species.

DETAILED DESCRIPTION OF THE INVENTION

Figure 1A:
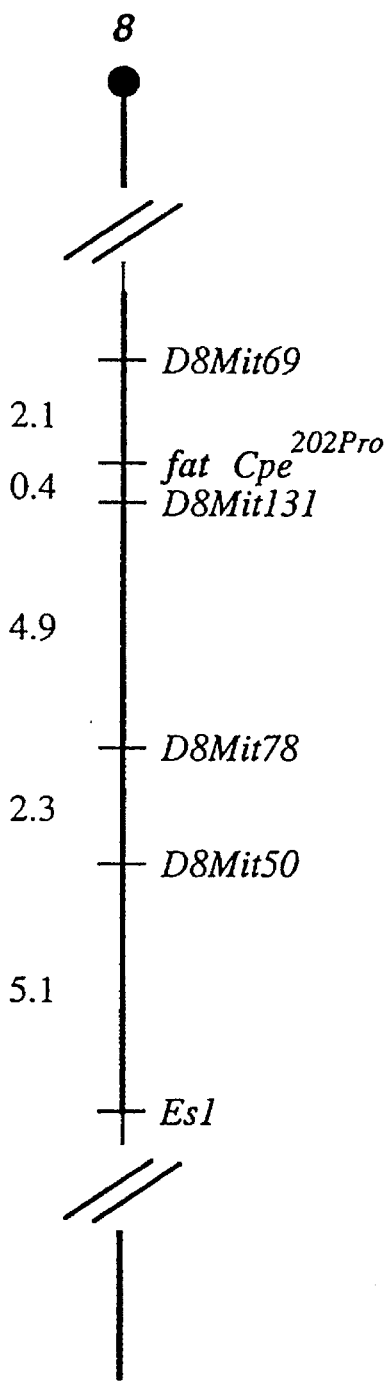
FIG. 1 fat was mapped to the proximal part of mouse Chromosome 8 by an intercross analysis (a) The partial Chromosome 8 linkage map shows the location of fat as well as the Cpe allele characteristic for BKS-fat/fat in relation to linked markers. Recombination distances in centiMorgans between loci are shown to the left of the chromosome. 400 phenotyped intercross mice were genotyped for the markers (except Es1 for which only 156 animals were typed). (b) Haplotypes in the genomic region around fat were established for all available obese animals that inherited a crossover between the markers D8Mit69 and D8Mit50. Open squares represent HRS homozygosity, shaded squares heterozygosity, and dark squares BKS homozygosity. This sample of 42 animals was drawn from a total of 1,400 intercross progeny. This analysis places fat in close proximity to Cpe between the markers D8Mit69 and D8Mit131.

The present invention is based on the discovery that a mutation in the carboxypeptidase E gene is responsible for impaired glucose tolerance or diabetes in a mammalian animal model system. Obesity is another clinical disorder demonstrated herein to be associated with a mutation in the carboxypeptidase E gene. The carboxypeptidase E gene product is known to cleave C-terminal amino acid residues from substrate proteins, and is a principal enzyme involved in the processing of precursor forms of peptide hormones into their mature, biologically active forms. The B-chain of insulin, immediately following the excision of the connector (C-) peptide from the proinsulin precursor by endopeptidase action, is a carboxypeptidase E substrate. The carboxypeptidase E activity is required to remove a diarginyl remnant of the C-peptide at the C-terminus of the insulin B chain. Without such removal, the C-terminal extended form has only a fraction of the activity of the processed form. Further, a defect in carboxypeptidase E activity leads to an accumulation of proinsulin which also has low biological activity.

The invention relates, in one aspect, to a method for identifying an individual afflicted with a clinical disorder Which is associated with a mutation in the carboxypeptidase E gene. Examples of such clinical disorders include diabetes, impaired glucose tolerance and obesity. With respect to diabetic syndromes, elevated levels of glucose in the plasma of such individuals result from reduced levels of biologically active insulin due to defective processing of the C-terminally extended form of insulin. The diagnosis of impaired glucose tolerance or diabetes is made through the application of objective diagnostic criteria (see e.g., *Harrison's Principles of Internal Medicine*, Isselbacher et al. (Eds.), McGraw-Hill, Inc. (New York), Thirteenth Edition (1994)).

There is general agreement on a diagnosis of diabetes when, for example, a patient presents symptoms attributable to osmotic diuresis associated with hyperglycemia. Similarly, there is general agreement that an asymptomatic patient with persistently high fasting glucose levels (i.e., at least two readings of greater than or equal to 7.8 mmol/L in venous plasma following overnight fasting) is diabetic. Diagnosis is more complicated in individuals suspected to be diabetic, but having normal fasting glucose levels. Such individuals are typically given an oral glucose tolerance test. If abnormal values are determined, a diagnosis of diabetes or impaired glucose tolerance is made. In 1979, the National Diabetes Data Group of the National Institutes of Health provided revised criteria for the diagnosis of diabetes following a challenge with oral glucose:

1) Fasting (overnight): Venous plasma glucose concentration $\geq 7.8$ mmol/L on at least two separate occasions.

2) Following ingestion of 75 g of glucose: Venous plasma concentration $\geq 11.1$ mmol/L at 2 hours after ingestion and on at least one other occasion during the 2 hour test. If the 2 hour value is between 7.8 and 11.1 mmol/L and one other value during the 2 hour test period is equal to or greater than 11.1 mmol/L, a diagnosis of impaired glucose tolerance is suggested.

To link the diagnosis of a clinical disorder with a mutation in the carboxypeptidase E gene, further experimentation is required. For example, such a linkage can be determined by isolating nucleic acid encoding carboxypeptidase E from cells of the individual and expressing the isolated nucleic acid by recombinant DNA techniques. The enzymatic activity of the expressed carboxypeptidase is then determined in an in vitro assay. Experimentation such as the in vitro activity is more than confirmatory in nature. Such experimentation is necessary to rule out the identification of a previously unknown wild-type allele.

The expression of eukaryotic genes by recombinant DNA techniques is complicated, relative to the recombinant expression of prokaryotic genes, by the presence of intervening sequences (called introns) which interrupt the coding sequence of the gene. The segments of an intron-containing eukaryotic gene which actually encode protein are referred to as exons. The mammalian carboxypeptidase E gene is an intron-containing gene.

A variety of techniques can be employed to express, by recombinant DNA techniques, an intron-containing gene of interest. In vivo, intron and exon sequences are transcribed into mRNA as a single transcription unit. Introns are subsequently spliced out by cellular enzymes to produce an mRNA encoding the full length gene product. A common recombinant DNA technique which is used to express an intron-containing eukaryotic gene involves the production of cDNA (copy DNA) from a spliced mRNA intermediate. Typically, poly(A)-containing mRNA is isolated from cells known to express the gene of interest. A poly(dT) primer is annealed to the poly(A) tail of mRNA and an RNA-dependent DNA polymerase (e.g., reverse transcriptase) is used to synthesize a first DNA strand which is complementary to the mRNA strand. Using the first DNA strand as template, second strand synthesis using a DNA-dependent DNA polymerase is used to produce double-stranded cDNA which is free of introns. If necessary, overlapping cDNA clones are linked to produce a full-length cDNA encoding the gene of interest.

Carboxypeptidase E is known to be expressed in highly specialized tissue including, for example, the brain and adrenal gland (see e.g., Manser et al., (*Biochem. J.* 267:517 (1990)). In light of the complex nature of such tissue, the isolation of mRNA from biopsy samples of a patient is not a viable option.

An alternative to the production of cDNA from an mRNA intermediate involves the use of intron-containing genomic DNA. Genomic DNA can be isolated from any cells from the individual. Particularly convenient cells for the isolation of genomic DNA are the peripheral white blood cells. Such cells can be isolated from the plasma of the individual, and genomic DNA is isolated using standard techniques (Maniatis et al., *Molecular Cloning*, Cold Spring Harbor Laboratory, Cold Spring Harbor, N.Y. (1989)).

The gene encoding carboxypeptidase E is known to be highly conserved in eukaryotic systems (see e.g., Manser et al., *Biochem. J.* 267:517 (1990)). A variety of techniques can be employed to isolate and clone a genomic DNA fragment from the individual which contains the carboxypeptidase E gene. A preferred method is to use the long range polymerase chain reaction (PCR) technique (Cheng et al., *Proc. Natl. Acad. Sci. USA* 91:5695 (1994)). This technique differs from the standard PCR technique in that a low level of a polymerase having exonuclease activity (for example, DNA Polymerase I) is included in the amplification mixture. The inclusion of this activity facilitates repair during the amplification process. Using this technique, amplification of the carboxypeptidase E locus (approximately 42 kb in length) can be accomplished. Opposing primers for this amplification can be designed following review of the 5' and 3' noncoding sequences from the known human cDNA sequence (Genbank Accession No. X51405; SEQ ID NO 1).

In an alternative to the long range PCR technique, a genomic DNA library can be screened using human DNA probes specific for carboxypeptidase E. Procedures for the construction of a genomic DNA library are well known in the art (see e.g., Maniatis et al., *Molecular Cloning*, Cold Spring Harbor Laboratory, Cold Spring Harbor, N.Y. (1989)). Suitable probes can be selected by reference to the human carboxypeptidase E cDNA sequence referred to above.

The isolated genomic DNA is then inserted into a eukaryotic expression vector. A variety of suitable vectors are available from commercial sources including, for example, pREP9, pRc/RSV, or pCEP4 (Invitrogen, San Diego, Calif.). Following transfection of eukaryotic cells (e.g., COS-7 cells) the carboxypeptidase E gene is transcribed into mRNA. Cellular enzymes will function to splice out introns and link together the exon sequences. The spliced mRNA product is then translated into biologically active carboxypeptidase E. As described in greater detail in the Exemplification section which follows, a eukaryotic expression system (baculovirus) was selected for initial expression experiments in light of the fact that the system is capable of glycosylating eukaryotic proteins (carboxypeptidase E is a glycoprotein). A eukaryotic system is also preferred in light of the fact that carboxypeptidase E is synthesized as an inactive precursor which is Subsequently processed to give rise to the active form.

If desired, cDNA can be produced by conventional techniques (see e.g., Maniatis et al., *Molecular Cloning*, Cold Spring Harbor Laboratory, Cold Spring Harbor, N.Y. (1989)) from the mRNA produced following transcription of the genomic DNA and processing of the mRNA. Following the isolation of cDNA encoding the enzyme, it will be recognized that it is a matter of routine experimentation to express carboxypeptidase E in a bacterial system to determine whether the nonglycosylated product is suitable for activity comparisons in an in vitro enzymatic assay of the type described below. Since the sequence of the mature form of carboxypeptidase E is known (see Genbank Accessing No. X51405 and SEQ ID NO. 2), it is possible to produce the active form by recombinant expression in the absence of eukaryotic processing enzymes. Methods for the production of proteins having N-terminal residues other than methionine by recombinant DNA techniques have been described in the literature (see, e.g., U.S. Pat. No. 5,132,213).

Provided that the ratio of detected enzyme activity levels observed in comparisons between wild-type carboxypeptidase E and a mutant form remain relatively constant (e.g., less than about 5%–10% deviation), any of the many eukaryotic or prokaryotic expression systems can be used to express carboxypeptidase E prior to carrying out in vitro enzyme assay studies. Those of skill in the art are familiar with the requirements of such expression systems, and a review of the vast body of literature is beyond the scope of this document.

Following incubation for a period of time sufficient for expression of the encoded carboxypeptidase E in the expression system selected, an in vitro enzymatic assay can be carried out to determine whether the carboxypeptidase E encoded by the DNA from the individual is characterized by a substantial reduction in the ability to cleave substrate relative to the wild-type counterpart which is produced in an otherwise identical manner. As used herein, a substantial reduction in the level of carboxypeptidase E activity from the individual, relative to that of wild-type carboxypeptidase E, is at least about 2-fold.

In vitro assay techniques for carboxypeptidase E activity have been reported in the literature (see e.g., Fricker, *Neuroprotocols: A companion to Methods in Neurosciences* 5:1–6 (1994)). More specifically, the cited article by Fricker describes two assays for determining carboxypeptidase E activity—one employs the dansyl fluorescent group whereas the other involves the use of a radioactive label as a reporter group. Both assays are sensitive, but do not provide the ability to distinguish activity attributable to the various peptide processing carboxypeptidases.

In the first of the two assays outlined in the preceding paragraph, the substrate dansyl-Phe-Ala-Arg has been determined to be an excellent substrate (see Fricker and Snyder, *J. Biol. Chem.* 258:10950 (1988)). A radioactive substrate which has been determined to be useful in connection with the detection of picogram quantities of carboxypeptidase E is [$^{125}$I]-acetyltyrosly-Ala-Arg (Fricker and Devi, *Anal. Biochem.* 184:21 (1990)). The basis for both assays is that the cleavage product, but not the uncleaved substrate, quantitatively partitions into an organic solvent. Thus, following incubation for a period of time sufficient for substrate recognition and cleavage (e.g., one hour or less is suitable), a chloroform extraction is carried out. Depending on the format of the assay either the fluorescence, or radioactivity, is determined by conventional techniques.

A second method for identifying an individual afflicted with a clinical disorder associated with a mutation in the carboxypeptidase E gene involves determining the nucleotide sequence of the DNA encoding carboxypeptidase E from the individual, and comparing the DNA sequence to the DNA sequence encoding a wild-type allele of carboxypeptidase E. The cDNA sequence encoding human wild-type carboxypeptidase E has been previously reported (see e.g., Manser et al., *Biochem. J.* 267:517 (1990); Genbank accession No. X51405). This DNA sequence corresponding to this sequence is represented below as SEQ ID NO. 1. A convenient method for determining the sequence of nucleotides in a DNA molecule is by the dideoxynucleotide termination method of Sanger et al., *Proc. Natl. Acad. Sci. USA* 74:5463 (1977)). With knowledge of the human carboxypeptidase E cDNA sequence, primers complementary to exon sequences can be designed. Given the high degree of conservation between mammalian carboxypeptidase E genes, one of skill in the art can predict intron locations. Using this information, a sequencing strategy can be developed. If necessary intron-specific primers can be designed using the data generated in the sequencing experiments.

If an alteration is detected in the carboxypeptidase E sequence from the individual being tested, relative to the known wild-type human sequence, it is highly likely that elevated glucose levels detected in the individual by the tests described above are a consequence of this mutation. This can, of course, be confirmed by repeating the expression and in vitro enzyme activity experiments discussed above. The preferred method for creating an expressible version of the mutant gene is to recreate the mutation by site-directed mutagenesis using the wild-type human cDNA clone as the starting construct.

Following the identification of a mutation in the carboxypeptidase E gene which results in a substantial decrease in the activity of enzyme, an oligonucleotide probe specific for this mutation can be designed and incorporated into a screening kit for the identification of the mutation. Typically such oligonucleotide probes have a length of from about 10 to about 50 nucleotides. Such a probe will hybridize, under stringent hybridization conditions, to the predetermined carboxypeptidase E mutant allele, but not to a wild-type allele. As used herein, stringent hybridization criteria refers to hybridization in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). In a typical hybridization format, the carboxypeptidase E encoding DNA is fixed to a solid support (e.g., nitrocellulose). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.).

Individuals identified as being afflicted with a clinical disorder such as impaired glucose tolerance, diabetes or obesity (using, for example, the methods described above, or any other method) can be treated therapeutically by introducing, into the plasma of the individual, an arginine carboxypeptidase which is characterized by the ability to remove a diarginyl C-terminal extension from the insulin B-chain under physiological conditions. Examples of such arginine carboxypeptidase enzymes include carboxypeptidase H (Grimwood et al., *J. Biol. Chem.* 264:15662 (1989)), carboxypeptidase M (Skidgel et al., *J. Biol. Chem.* 264:2236 (1989)), carboxypeptidase N (Ito et al., *Enzyme* 42:8 (1989); Grimwood et al., *J. Biol. Chem.* 263:14397 (1988)), carboxypeptidase U (Hendriks et al. *Biochem. Biophys. Acta* 1034:86 (1990)) and carboxypeptidase B (Pascual et al., *Eur. J. Biochem.* 179:609 (1989)). The references cited in connection with each of the listed enzymes describe methods for their isolation. Carboxypeptidase E is not highly active at physiological pH.

As discussed in greater detail in the Exemplification section which follows, the hyperinsulinemia associated with impaired glucose tolerance or diabetes resulting from defective carboxypeptidase E is actually hyperproinsulinemia which results from the reduced ability to remove a diarginyl C-terminal extension from the insulin B-chain. Therefore, the introduction into the plasma of an individual of a molecule being characterized by the ability to remove a diarginyl C-terminal extension from the insulin B-chain functions to complement the carboxypeptidase E mutation by providing an activity which results in the production of the fully active form of insulin.

With respect to diabetic syndromes, although the introduction of insulin directly offers an alternative treatment (the treatment used prior to this invention for that percentage of diabetics whose affliction results from a mutation in the carboxypeptidase E gene), the use of an enzyme which removes the diarginyl C-terminal extension from the insulin B-chain offers at least one significant advantage. More specifically, maintaining proper insulin levels by injection of insulin directly is extremely difficult due to the interplay of various feedback controls. For example, after a meal is eaten, a prompt rise in insulin release occurs (C-terminally extended insulin in the case of a defective carboxypeptidase E gene). The presence of an exogenously added processing activity in plasma which functions to remove the diarginyl C-terminal extension from the insulin B-chain creates a system which more closely approximates the control mechanisms of a healthy individual. The presence of this activity would result in a spike in insulin levels after a meal due to increased substrate concentration in plasma.

In a preferred embodiment, the molecule which removes a diarginyl C-terminal extension from the insulin B-chain is introduced into the plasma by subcutaneous injection or infusion. The formulation containing the processing enzyme is introduced in quantities calibrated to maintain a venous plasma glucose concentration level which is less than the criteria established for the diagnosis of diabetes or impaired glucose tolerance (discussed above).

The expression "introducing into the plasma" of the individual an arginine carboxypeptidase which is characterized by the ability to remove a diarginyl C-terminal extension from the insulin B-chain under physiological conditions is also intended to encompass the introduction of the molecule into the plasma by gene therapy protocols. Using such techniques, any cell from the individual capable of secreting a protein into plasma can be used for transfection experiments. Preferred cells for gene therapy protocols are bone marrow cells. Such cells can be isolated from the individual, transfected with an appropriate vector, and reintroduced into plasma. An expressible copy of the gene encoding the molecule which removes a diarginyl C-terminal extension from the insulin B-chain is introduced into a vector capable of tranfecting such cells. So long as an appropriate signal sequence exists, or is provided by conventional techniques, the encoded product would be secreted into the plasma of the individual where it could catalyze the removal of the diarginyl C-terminal extension from the insulin B-chain.

The vector can be either a retroviral vector, adenoviral vector, another viral vector, or simply naked DNA within a gene delivery system, for example, a liposome-based delivery system. Both viral vectors and liposome-based gene delivery systems have been successfully used in approaches to gene expression in whole animals. Several types of vectors for gene therapy and other applications are already available (reviewed by Yee et al., *Proc. Natl. Acad. Sci. USA* 91:9564 (1994); see also Mulligan, *Science* 260:926 (1993) and Anderson, *Science* 256:808 (1992)). These vectors can be used for the delivery of a molecule having the ability to remove a diarginyl extension from the insulin B-chain in cell cultures, in whole animals, and, with appropriate preliminary testing, in human patients as well. Recent advances in the design of viral and plasmid-based vectors (see e.g., Nabel et al., *Proc. Natl. Acad. Sci. USA* 90:11307 (1993) and Mulligan, *Science* 260:926 (1993)) resulted in tailor-made, nonreplicating vectors that can transfect both growing and quiescent cells, and are either specific for cells that bear a predetermined surface marker or almost nonselective. Such vectors, in use for gene therapy and other applications (for example, Mulligan, *Science* 260:926 (1993) and Anderson, *Science* 256:808 (1992)), are powerful vehicles for the delivery of a gene of interest.

EXEMPLIFICATION

The mouse autosomal recessive mutation fat (fat) arose on the inbred HRS/J (HRS) strain and was characterized by Coleman and Eicher (Coleman, D. L. and Eicher, E. M., *J. Hered.* 81:424 (1990)) as exhibiting a chronic hyperinsulinemia from weaning, followed by post-pubertal development of obesity without hyperglycemia. More recently, the mutation has been backcrossed onto C57BLKS/J (BKS), an inbred strain which develops hyperglycemia when the mice are homozygous for either of two other unlinked obesity-inducing mutations, diabetes (db) and obese (ob) (Coleman, D. L., *Diabetologia* 14:141 (1978)). In generations past N6, development of maturity-onset hyperglycemia, primarily in males, has been observed (Leiter et al., *Diabetes* 40:1360 (1991)). However, unlike the diabetes syndromes in BKS-db/db and BKS-ob/ob mice, where plasma insulin levels decline with the onset of severe diabetes, radioimmunoassay of plasma revealed that BKS-fat/fat mice of both sexes maintained chronically high levels of plasma insulin independently of the onset of hyperglycemia (Leiter et al., *Diabetes* 40:1360 (1991)).

The fat mutation had been previously mapped to chromosome 8 (Paigen, B. J. and Coleman, D. L., *Mouse*

*Genome* 86:240 (1990)), unlinked to the two mouse insulin genes that are located on chromosomes 7 and 19. The map position of fat has now been refined in relation to a candidate gene, carboxypeptidase E (Carboxypeptidase E). The experiments which follow demonstrate that a missense mutation in Carboxypeptidase E is associated with the virtual absence of enzyme activity in islets and pituitary. This loss of exopeptidase function correlates with an aberrant increase in proinsulin and partially processed intermediates in both β-cells and in serum.

Results

Juxtaposition of Fat and Cpe Genes

Figure 1B:
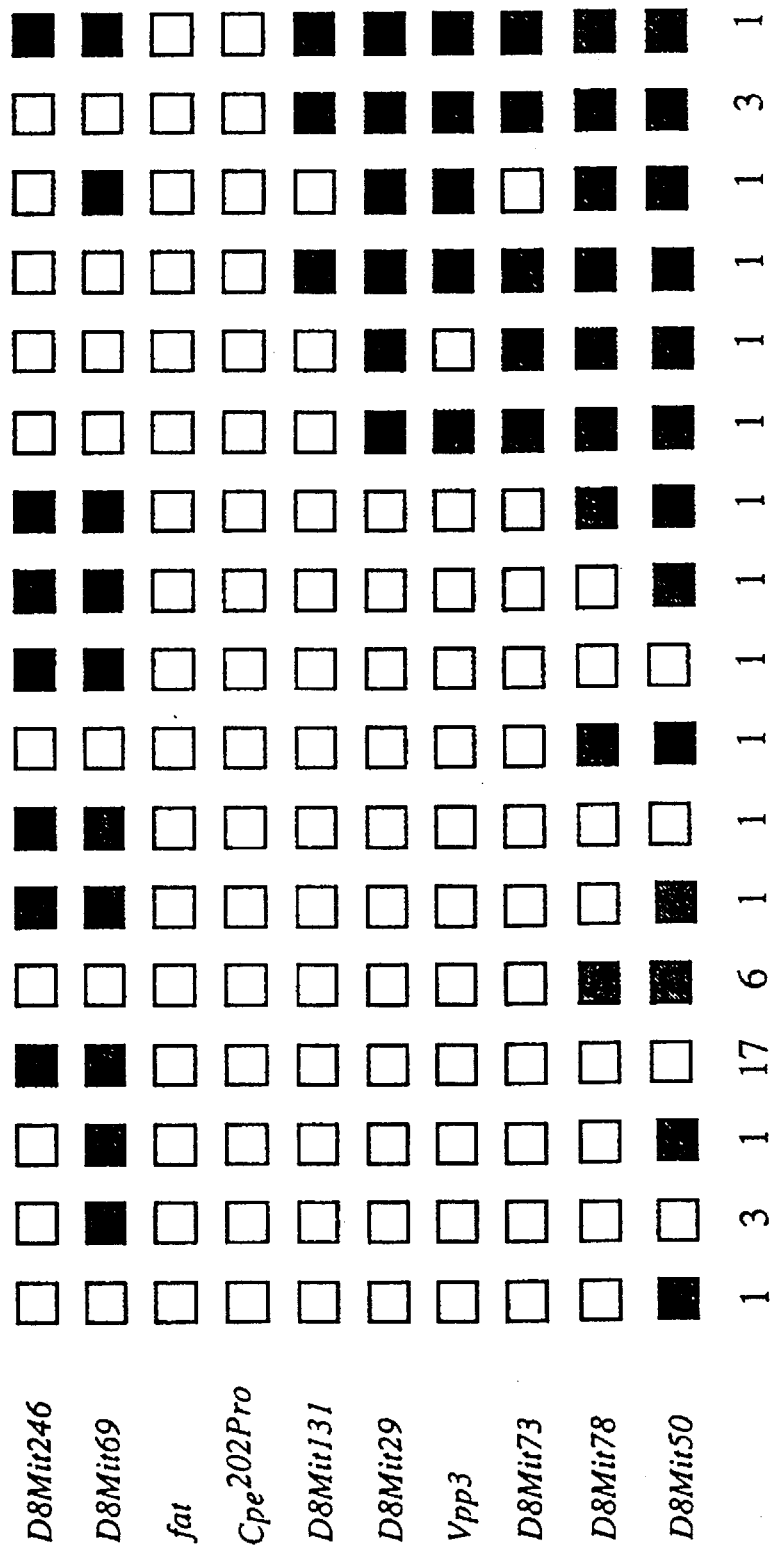

The chromosomal location of fat was determined by screening for recombinants in progeny of +/fat matings (FIG. 1). Because fat had arisen on the HRS strain and was backcrossed for five generations to the unrelated BKS strain, crossover events in the breeding colony can be identified. The fat mutation had provisionally been mapped 5 cM centromeric of esterase-1 (Es1) (Paigen, B. J. and Coleman, D. L., *Mouse Genome* 86:240 (1990)). To refine the map position, simple sequence repeat polymorphism (SSLP) markers (Dietrich et al., *Nature Genetics* 7:220 (1994)) were used to type DNA from obese progeny of +/fat matings to establish their haplotypes. This preliminary analysis indicated that fat must lie between the markers D8Mit69 and D8Mit50. Pedigrees were selected that had obese offspring homozygous for the flanking HRS alleles as well as lean offspring homozygous for the flanking BKS alleles in roughly the expected frequency. Four hundred mice from generations N6F12 to N7F4 were included in the mapping. Because the biochemical evidence described below indicated the Cpe might be a candidate gene for fat, a sequence polymorphism in exon 4 was used to map Cpe (formerly designated Cph-1) in this cross as well. A subset of animals was also typed for Es1, the marker relative to which fat was mapped originally. The number of mice with recombinant chromosomes compared to the total number of mice analyzed for each marker pair and the most likely gene order are: centromere—D8Mit69—(17/400)—fat—(0/400)—Cpe—(7/400)—D8Mit131—(39/400)—D8Mit78—(18/400)—D8Mit50—(16/156)—Es1, with genetic distance (±SE) of D8Mit69—(2.1±0.5 cM)—fat—(0.0±0.0 cM)—Cpe—(0.4±0.2 cM)—D8Mit131—(4.9±0.8 cM)—D8Mit78—(2.3±0.5 cM)—D8Mit50—(5.1±1.3)—Es1. A partial map of mouse chromosome 8 with the mapped loci and interlocus distances is shown in FIG. 1a. To further refine the map location of fat, we assembled haplotypes of phenotypically obese mice from the fat colony that had inherited a crossover between D8Mit69 and D8Mit50. This cohort of 42 mice was drawn from a total of 1,400 intercross progeny. Nine markers that showed an allelic difference between BKS and HRS were typed. The haplotypes observed are shown in FIG. 1b. It can be seen that, in individual mice, areas of HRS and BKS homozygosity alternate with heterozygosity, a consequence of the fact that the BKS-fat/fat stock is an incipient congenic strain. It also can be seen that the minimal area where all the obese animals are homozygous for HRS alleles is between the markers D8Mit69 and D8Mit131. No crossover was observed between fat and Cpe placing Cpe within 0.08 cM of fat, assuming the crossovers are evenly distributed in the interval between D8Mit69 and D8Mit131.

Proinsulin→Insulin Processing is Disturbed in Fat/Fat Mice

Figure 2:
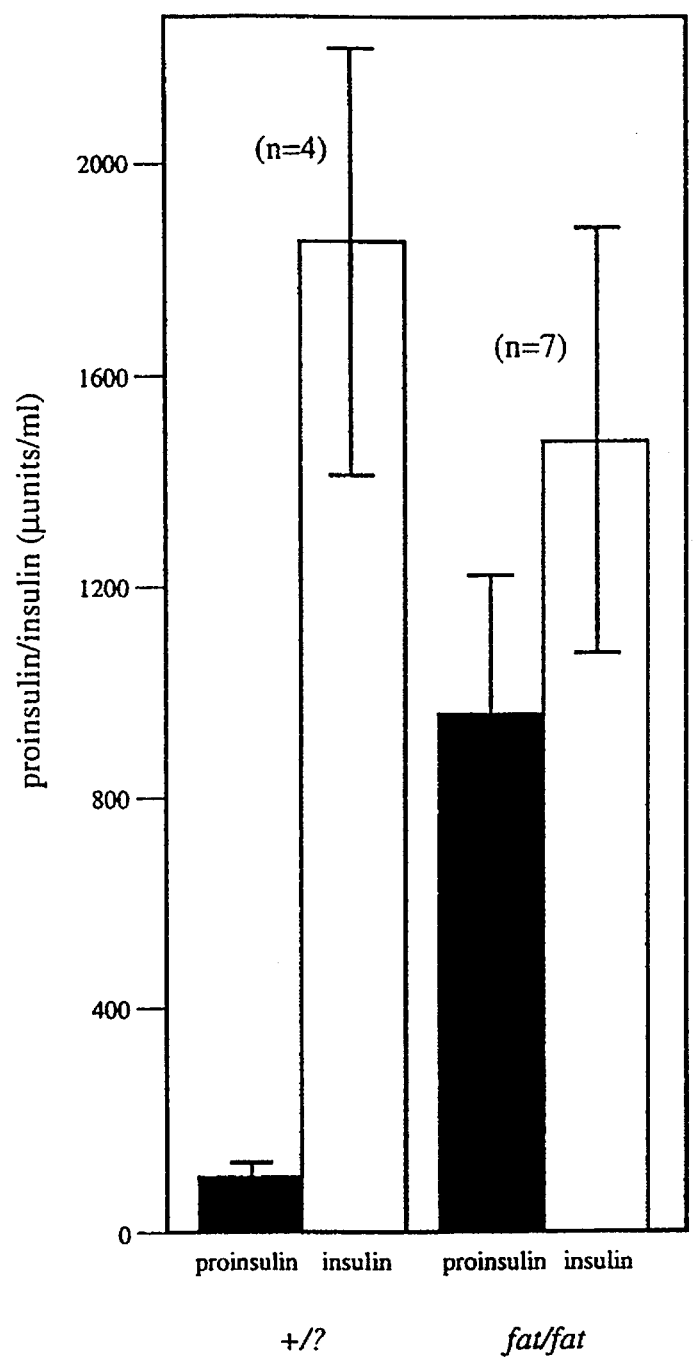
FIG. 2 Normoglycemic BKS-fat/fat 24–38-wk-old females (n=7) show a significantly (p<0.001) increased level of pancreatic proinsulins (open bars) versus insulins (filled bars) compared to lean females (n=4; mean of 2+/+ and 2+/fat donors). Data are mean±SEM.

Since BKS-fat/fat mice have high levels of insulin in plasma as detected by radioimmunoassay, it was not expected that hyperglycemic BKS-fat/fat males would be responsive to exogenous porcine insulin. In fact, these hyperglycemic mice were extremely sensitive to an i.p. injection of 2U of porcine insulin, with plasma glucose values dropping from >600 mg/dl to <100 mg/dl within 2 hr. Similarly, hyperglycemic BKS-fat/fat males receiving subcutaneous implants of osmotic minipumps (Alza, Palo Alto, Calif.) calibrated to deliver 1U of porcine insulin/24 hr remitted to normoglycemia within a week. This paradoxical insulin sensitivity in the face of high endogenous insulin immunoreactivity suggested that the endogenous insulins must be partially defective. The insulin-related compound in pancreases of normoglycemic fat/fat females and control littermates were extracted in acidified ethanol, fractionated by Biogel P-30 column chromatography, and the eluate radioimmunoassayed. Proinsulins/insulins in pooled serum samples were similarly extracted and analyzed. Analysis of pancreatic proinsulins/insulins (FIG. 2) showed a significant increase ($p<0.001$) in the ratio of proinsulins to insulins (from approximately 5% in controls to 66% in mutants). Column chromatographic analysis of the immunoreactive "insulin" in serum indicated that approximately 77% was proinsulin, thus accounting for its reduced biologic potency. Immunoreactive insulin-like material in serum of the fat/fat females, shown in FIG. 2, ranged between 675–1350 μU/ml in comparison to 19–31 μU/ml in +/fat controls. HPLC analysis of the insulin fraction from fat/fat female pancreas showed that a significant amount of the material eluted earlier than did standards of insulin I and II or the insulin fraction from pancreases of heterozygous control mice. Digestion of the material with carboxypeptidase B, which has the same specificity for C-terminal basic residues as CPE, converted these additional peaks into material that then eluted with the same retention time as insulin I and II. This result indicated the presence of increased quantities of B chain-extended (31,32)diarginyl insulin in fat/fat pancreas.

Further evidence of impaired proinsulin processing was provided by electron microscopy. In contrast to an abundance of mature β-granules with electron dense cores in +/+ controls, fat/fat β-cells exhibited a preponderance of the more electron-lucent immature granule forms known to be enriched for both proinsulin and the prohormone convertases (Orci et al., *Cell* 42:671 (1985); Steiner et al., *J. Biol. Chem.* 267:23435 (1992)).

The Fat Mutation is Associated with Loss of Enzymatically Active CPE in Pancreatic Islets and Pituitary Extracts.

Figure 3:
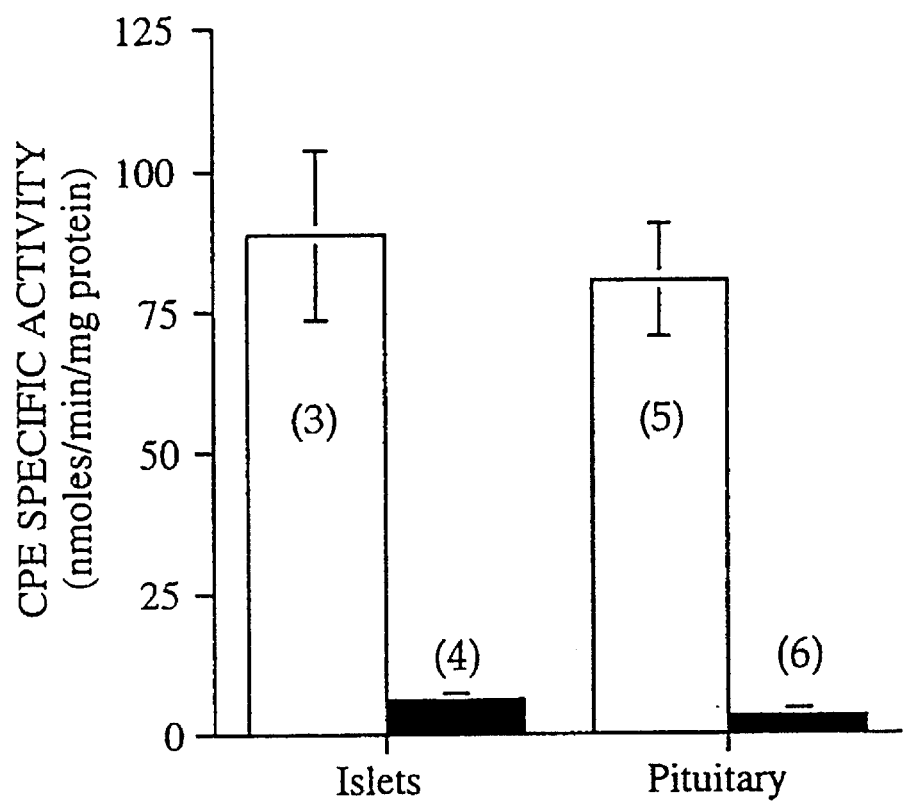
FIG. 3 Pancreatic islet and pituitary CPE activity and protein levels are severely reduced in fat/fat males compared to lean littermate controls. All tissue donors were >1.5 yr old, and fat/fat males were normoglycemic when necropsied. Carboxypeptidase E specific activities were determined in islet and pituitary extracts from normal (open bars) and fat/fat males (dark bars) assayed individually. Data are mean±SEM (n).

The function of CPE (also called CPH) in β-cells is to trim the carboxyterminal arginine residues from the products of endoproteolytic cleavage such as (31,32)diarginyl insulins (Davidson, H. W. and Hutton, J. C., *Biochem. J.* 245:575 (1987); Rhodes, C. J. and Alarcón, C., *Diabetes* 43:511 (1994)). An examination of CPE enzymatic activity showed an approximately 20-fold decrease not only in collagenase-isolated islets, but also in pituitaries of fat/fat males compared to lean littermate controls (FIG. 3). Enzyme activity in extracts of islets and extracts from mutant females were similarly low. Western blot analysis of pancreatic islet and pituitary lysates shows a virtual absence of immunoreactive carboxypeptidase protein in mutant mice, but not in control mice. The Western blot analysis was performed several times with samples from both males and females, with similar results. This contrasts with the Western blot results obtained for the prohormone convertases PC1/3 and PC2, as well as granule amidating enzyme associated with prohormone processing, peptidylglycine α-amidating monooxygenase, which were present in equal amounts in the lysates of both genotypes.

Northern blot analysis employing a rat cDNA probe, however, revealed no differences in the amount of Cpe mRNA between fat/fat and +/+ animals, indicating that the CPE defect must be translational or posttranslational.

A Missense Mutation in the Cpe$^{fat}$ Allele

The biochemical data and the genetic proximity of fat and Cpe made Cpe an attractive candidate gene for fat. Several overlapping Cpe cDNA fragments were obtained by RT-PCR of total RNA extracted from BKS-fat/fat pancreatic islets and determined the coding sequence with an average coverage greater than three fold. The inferred amino acid sequence is, with one exception, in agreement with the published sequence for the homologous rat protein carboxypeptidase E (Jung et al., Mol. *Endocrinol.* 5:1257 (1991)). We found a total of 19 discrepancies between our sequence and the mouse Cpe cDNA sequence published in Genbank (accession #X61232). With one exception our sequence agrees with those from human and/or rat, and bovine Cpe cDNA in all 11 cases where changes in the predicted amino acid are involved. The one consistent difference to all published Cpe sequences was a transition from $^{729}$T to C (numbering based on $^1$ATG). This would change amino acid $^{202}$serine (TCT) to proline (CCT). The numbering system employed is based on that for carboxypeptidase A and B, in which amino acid 1 is defined as the N-terminal residue after removal of the propeptide. To confirm this finding, PCR primers that amplified the corresponding exon (exon 4) of the genomic sequence were constructed and the PCR products obtained by amplifying DNA and BKS, HRS, as well as all obese animals from our haplotype panel (FIG. 1b), were sequenced. Both BKS and HRS sequences code for $^{202}$Ser which, together with a 13 amino acid motif surrounding it, is conserved in the Cpe protein from human (Manser et al., *Biochem. J.* 267:517 (1990)), rat (Fricker et al., *Mol. Endocrinol.* 3:666 (1989)), bovine (Fricker et al., *Nature* 323:461 (1986)), and fish (Roth et al., *Mol. Cell. Endocrinol.* 78:171 (1991)) (FIG. 4). By contrast, all the obese animals from our mapping, as well as from the haplotype panel, code for proline in this position.

To confirm that the $^{202}$serine to proline mutation was responsible for the absence of CPE activity in the fat/fat mouse, this mutation was created in rat CPE and the protein expressed in the baculovirus system. Based on the sequence analysis of mouse CPE, there are only 2 amino acid differences between rat and mouse CPE within the mature form of the enzymes (99.5% identity) and both of these differences are conservative substitutions ($^{95}$Arg vs $^{95}$Lys, and $^{373}$Val vs $^{373}$Ala). When wild-type CPE ($^{202}$serine) is expressed in the Sf9 cells, 2 bands of immunoreactive CPE are detected, presumably corresponding to proCPE and CPE. The $^{202}$proline mutant also shows two bands of immunoreactivity although the levels of immunoreactive CPE are slightly lower for the mutant, as compared to wild-type CPE. Western blot analysis using antisera directed against the N-terminal region of CPE gave results comparable to those with the C-terminally-directed antisera. immunoreactive CPE was not detected with cells infected with wild-type virus. Similar analysis of the media from infected cells shows immunoreactivity only for the wild-type CPE, and not for the $^{202}$proline mutant CPE or the negative control. Analysis of the CP enzymatic activity in the cell extracts showed a high level of activity only for the cells infected with wild-type CPE, and not for the other groups of cells. The level of CP activity in the cells infected with the $^{202}$proline mutant CPE is comparable to the level of CP activity in cells infected with control virus. This background activity presumably represents cellular enzymes other than CPE, which are detected by the enzyme assay. CPE activity was also detected in media from cells infected with $^{202}$serine CPE, but not from cells infected with $^{202}$proline CPE.

Methodology

Mice. BKS-fat/fat mice were produced by mating BKS-+/fat heterozygous males to C.B-17/J-scid/scid or NOD/LtSz-scid/scid females transplanted with ovarian grafts from BKS-fat/fat females. Mice were maintained on a 14 hr:10 hr light-dark cycle in a temperature and humidity controlled vivarium. They were allowed free access to acidified drinking water and chow (Old Guilford 96WA, Emory Morse Co., Guilford, Conn.). Mice were weighed at weekly intervals; mutants were detected by their visually obese phenotype developing between 8–16 wk of age. Plasma glucose was determined at monthly intervals, beginning at 6 wk of age. Insulin radioimmunoassay in plasma was performed using a kit (Linco, St. Louis, Mo.) and rat insulin standards. Pancreatic islets were isolated by inflation of the common bile duct with a collagenase solution (Boehringer-Mannheim, Indianapolis, Ind.) and hand-picked under a dissecting microscope. Acid ethanol extraction of pancreatic (pro) insulin, and procedures for electron microscopy, were as previously described (Leiter, E. H., *Am. J. Pathol.* 119:22 (1985)).

Chromosomal mapping.

Progeny for mapping were generated by intercrossing C57BLKS/J-fat/+mice. A total of 400 mice were used to map the fat locus. fat was initially typed as homozygous HRS for obese progeny and "not HRS" for slim animals. After initially determining gene order, all slim animals that did not show a crossover between the flanking markers D8Mit69 and DSMit78 were assigned the genotype of these markers. Cpe alleles were determined by sequencing Cpe exon 4 in all animals that showed a crossover between D8Mit69 and D8Mit50. SSLP primers were purchased from Research Genetics (Huntsville, Ala.). A haplotype analysis was performed on a cohort of 42 obese progeny that showed a crossover event between the markers D8Mit69 and D8Mit50. These mice were found among 1,400 progeny of the same intercross. PCR amplification was from 50 ng of genomic DNA, primer and deoxynucleotide concentrations were 200 nM and MgCl$_2$ was 1.5 mM. Cycling conditions were: 2 min 95° C. initial denaturation, followed by 48 cycles of 10 sec at 94° C., 20 sec at 48°0 C. and 40 sec at 72° C. followed by a final extension of 10 min at 72° C. PCR products were analyzed electrophoretically on 3% Metaphor (FMC, Rockland, Me.)/1% agarose gels. Vpp3 alleles were typed as a conformational polymorphism in a Vpp3 intron that was PCR amplified using the primers: F8 5'- TGTCGC-CAGGCTGGTTTGG -3' (SEQ ID NO 3) and R10 5'-TAAACAGGCAAGCTCTCTTCC -3' (SEQ ID NO 4). DNA from heterozygous fat/+ animals yields two DNA fragments of 500 and 510 bps respectively on a 2% agarose gel; both homozygous BKS and HRS yield one 500 bp fragment. Esterase-1 alleles were determined by agarose gel electrophoresis as described (Prochazka et al., *Diabetes* 41:98 (1992)). Recombination distances and gene order were determined using the computer program MAPMAKER (Lander et al., *Genomics* 1:174 (1987)). Standard errors for recombination distances were calculated using the computer program MAPMANAGER (Manley, K. A., *Mamm. Genome* 4:301 (1993)).

HPLC analysis of mutant insulins.

Acid-ethanol extracts of pancreases from normal and mutant mice were prepared and then subjected to Biogel P30 chromatography in 3M acetic acid as described elsewhere (Tager et al., *Methods in Enzymology:* 326 (1975)). The fractions containing insulin were combined, evaporated to dryness, and analyzed by reverse phase HPLC using a Bydac C-4 column (10µ particle size, 250×4.6 mm I.D.) eluted at 1.0 ml/min with a linear acetonitrile gradient (27–32%) in 0.1% TFA during 60 min.

CPE enzymatic assay and Western blotting.

CPE was measured fluorimetrically at pH 5.0 in the presence of 1 mM $CaCl_2$ using the substrate dansyl-Phe-Ala-Arg as described (Fricker, L. D., *Methods in Neuroscience* 23:237 (1995)). CP activity that was not due to CPE was determined from parallel assays conducted in the presence of 1 μM guanidinoethylmercapto-succinic acid (GEMSA), a selective CPE inhibitor. This activity was substracted from total activity (per mg protein determined by the Bradford assay) to obtain CPE specific activity. Western blot analysis was performed on 50 μg of protein from lysates of 575 islets pooled from 3 24-wk-old fat/fat female donors and from 589 islets pooled from 4 age matched +/+ donors. Pituitaries from the same donors were frozen on dry ice, and lysed in 1 ml volumes of PBS containing 0.1% Triton X-114, 1000 U/ml aprotinin, 200 μM leupeptin, 0.2 mM phenylmethylsufonyl fluoride, and 0.5 mM dithiothreitol. 50 μg samples were electrophoresed through a 12% denaturing polyacrylamide gel and transferred onto a nylon membrane. The membrane was probed with a rabbit antiserum directed against the N-terminal region of CPE as described previously (Fricker et al., *J. Biol. Chem.* 265:2476 (1990)) using the enhanced chemoluminescence detection method (Amersham, Arlington Heights, Ill.). CPE is typically present in multiple forms with MW ranging between 50–56 KDa.

RT-PCR amplification and sequence analysis.

cDNA fragments were generated by reverse transcription and polymerase chain reaction amplification of BKS-fat/fat RNA. Total pancreas RNA was reverse transcribed using Superscript II reverse transcriptase (Gibco BRL, Gaithersburg, Md.) primed with oligo$(dT)_{12-18}$ and the product RNAse H digested according to manufacturer's instructions. One tenth volume of the first strand reaction was used to amplify Cpe cDNA using rTth XL DNA polymerase (Perkin Elmer, Norwalk, Conn.) and Cpe specific oligonucleotide primers. Full length coding sequence was amplified using the primers F6: 5'- CAGTGCAGCTCGCGGGAC -3' (SEQ ID NO 5) and R5: 5'- AAGCGAATGTTGATGTAGAATG -3' (SEQ ID NO 6). Internal fragments were obtained using the primer pairs F8: 5'- CCTGATGACGCAATTTTCC -3' (SEQ ID NO 7) and R5; F6: 5'- CAGTGCAGCTCGCGGGAC -3' (SEQ ID NO 8) and R1: 5'- TCCAGGTCTGGGAAGTTAC -3' (SEQ ID NO 9); and F1: 5'- AGTACCAGAAAGGCAATGAG -3' (SEQ ID NO 10) and R5. Primers and deoxynucleotides were used at concentrations of 200 nM; $MgCl_2$ was present at 1.5 mM. Cycling conditions were: 2 min 95° C. initial denaturation, followed by 48 cycles of 5 sec at 94° C., 10 sec at 50° C. and 2 min at 72° C. Final extension was 10 min at 72° C. After electrophoresis in low melting point agarose, >95% of the product was present in single bands of the expected size. The bands were cut out and DNA was isolated by agarase treatment (Epicenter Technologies, Madison, Wis.). The fragments were sequenced by dideoxy cycle sequencing either manually (Sequitherm Kit, Epicenter Technologies, Madison, Wis.) or automatically (Prism, Applied Biosystems, Foster City, Calif.). In addition to the above primers, 7 more oligonucleotides were selected from the published mouse cDNA sequence (Genbank #X61232) so that an average coverage of greater than three fold was obtained. Cpe exon 4 (containing the fat mutation) was amplified from 50 ng of genomic DNA from BKS, HRS and 66 fat/fat and fat/+ recombinant mice. Primers used were F14: 5'- GGAACAGCTTGCCCCCGAG -3' (SEQ ID NO 11) and R14: 5'- TACCGCTCCGTGTCTCATC -3 (SEQ ID NO 12). Primer and deoxynucleotides concentrations were 200 nM and 1.5 mM, respectively. Cycling conditions were: 2 min 95° C. initial denaturation, followed by 36 cycles of 10 sec at 94° C., 20 sec at 52° C. and 40 sec at 72° C., followed by a final extension of 10 min at 72° C. The DNA fragments were gel isolated and manually sequenced.

Baculovirus Expression

A 2 kb cDNA fragment containing the entire coding region of rat CPE was subcloned into the pAlter-1 vector (Promega, Madison, Wis.). An oligonucleotide encoding the $^{202}$serine to proline mutation (TCT to CCT) was used in conjunction with an oligonucleotide to mutate the ampicillin sensitive gene in the pAlter-1 vector to an ampicillin resistant gent (Promega, Madison, Wis.). After selection of the recombinants using ampicillin-containing plates, the plasmid was purified from one recombinant and the mutation confirmed by sequence analysis. Both wild-type rat CPE cDNA and rat CPE cDNA with the $^{202}$proline mutation were subcloned into the pVL1393 baculovirus expression vector (Pharminogen, San Diego, Calif.). Recombinant baculovirus was then generated using the Baculogold system (Pharminogen, San Diego, Calif.), as described by the manufacturers. For the infection, $10^8$ Sf9 cells in 100 ml of Sf900-II (GIBCO, Gaithersburg, Md.) were Combined with approximately $5 \times 10^8$ plaque-forming units of virus in 500 ml flasks, and the cells were cultured for 72 hours in an orbital shaker at 27° C. Following this incubation, cells were isolated by centrifugation at 200×g for 5 minutes. The cells were combined with 20 ml phosphate buffered saline and frozen. For the analysis of CPE, the cells were thawed, sonicated for 20 seconds, and then aliquots taken for enzymatic determinations.

We claim:

1. A method for identifying a clinical disorder associated with a mutation in the carboxypeptidase E gene, the method comprising:

a) isolating DNA encoding carboxypeptidase E from the individual;

b) expressing the isolated DNA encoding carboxypeptidase E using recombinant DNA techniques; and c) determining the enzymatic activity of the expressed carboxypeptidase E and comparing the determined activity to that determined for wild-type carboxypeptidase E which is produced and assayed in an otherwise identical manner, a substantial reduction in the enzymatic activity relative to that of wild-type being indicative of the clinical disorder associated with a mutation in the carboxypeptidase E gene, the clinical disorder being selected from the group consisting of obesity, diabetes or impaired glucose tolerance associated with aberrant insulin processing.

2. The method of claim 1 wherein a substantial reduction in the enzymatic activity is at least about 2-fold.

3. The method of claim 1 wherein the DNA is isolated from peripheral white blood cells.

4. The method of claim 3 wherein the isolated DNA is expressed in an expression system capable of glycosylating proteins.

5. The method of claim 4 wherein the expression system is a baculovirus-based expression system.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2443 base pairs
        ( B ) TYPE: nucleic acid
        ( C ) STRANDEDNESS: single
        ( D ) TOPOLOGY: linear ( i i ) MOLECULE TYPE: mRNA ( i x ) FEATURE:
    ( A ) NAME/KEY: CDS
    ( B ) LOCATION: 414..1721

( x i ) SEQUENCE DESCRIPTION: SEQ ID NO:1:

| | | | | | | |
|---|---|---|---|---|---|---|
| AAATGGCGTG | CCCGTCTCTC | CGCCGGCCCC | CTGCCTCGCA | GTGGTTTCTC | CTGCAGCTCC | 60 |
| CCTGGGCTCC | GCGGCCAGTA | GTGCAGCCCG | TGGAGCCGCG | GCTTTGCCCG | TCTCCTCTGG | 120 |
| GTGGCCCCAG | TGCGCGGGCT | GACACTCATT | CAGCCGGGGA | AGGTGAGGCG | AGTAGAGGCT | 180 |
| GGTGCGGAAC | TTGCCGCCCC | CAGCAGCGCC | GGCGGGCTAA | GCCCAGGGCC | GGGCAGACAA | 240 |
| AAGAGGCCGC | CGCGTAGGA | AGGCACGGCC | GGCGGCGGCG | GAGCGCAGCG | ATGGCCGGGC | 300 |
| GAGGGGGCAG | CGCGCTGCTG | GCTCTGTGCG | GGGCACTGGC | TGCCTGCGGG | TGGCTCCTGG | 360 |
| GCGCCGAAGC | CCAGGAGCCC | GGGGCGCCCG | CGGCGGGCAT | GAGGCGGCGC | CGG CGG | 416 |

```
                                                                                       Arg
                                                                                        1

CTG  CAG  CAA  GAG  GAC  GGC  ATC  TCC  TTC  GAG  TAC  CAC  CGC  TAC  CCC  GAG        464
Leu  Gln  Gln  Glu  Asp  Gly  Ile  Ser  Phe  Glu  Tyr  His  Arg  Tyr  Pro  Glu
               5                        10                       15

CTG  CGC  GAG  GCG  CTC  GTG  TCC  GTG  TGG  CTG  CAG  TGC  ACC  GCC  ATC  AGC        512
Leu  Arg  Glu  Ala  Leu  Val  Ser  Val  Trp  Leu  Gln  Cys  Thr  Ala  Ile  Ser
                    20                       25                       30

AGG  ATT  TAC  ACG  GTG  GGG  CGC  AGC  TTC  GAG  GGC  CGG  GAG  CTC  CTG  GTC        560
Arg  Ile  Tyr  Thr  Val  Gly  Arg  Ser  Phe  Glu  Gly  Arg  Glu  Leu  Leu  Val
          35                       40                       45

ATC  GAG  CTG  TCC  GAC  AAC  CCT  GGC  GTC  CAT  GAG  CCT  GGT  GAG  CCT  GAA        608
Ile  Glu  Leu  Ser  Asp  Asn  Pro  Gly  Val  His  Glu  Pro  Gly  Glu  Pro  Glu
50                       55                       60                       65

TTT  AAA  TAC  ATT  GGG  AAT  ATG  CAT  GGG  AAT  GAG  GCT  GTT  GGA  CGA  GAA        656
Phe  Lys  Tyr  Ile  Gly  Asn  Met  His  Gly  Asn  Glu  Ala  Val  Gly  Arg  Glu
                         70                       75                       80

CTG  CTC  ATT  TTC  TTG  GCC  CAG  TAC  CTA  TGC  AAC  GAA  TAC  CAG  AAG  GGG        704
Leu  Leu  Ile  Phe  Leu  Ala  Gln  Tyr  Leu  Cys  Asn  Glu  Tyr  Gln  Lys  Gly
               85                       90                       95

AAC  GAG  ACA  ATT  GTC  AAC  CTG  ATC  CAC  AGT  ACC  CGC  ATT  CAC  ATC  ATG        752
Asn  Glu  Thr  Ile  Val  Asn  Leu  Ile  His  Ser  Thr  Arg  Ile  His  Ile  Met
          100                      105                      110

CCT  TCC  CTG  AAC  CCA  GAT  GGC  TTT  GAG  AAG  GCA  GCG  TCT  CAG  CCT  GGT        800
Pro  Ser  Leu  Asn  Pro  Asp  Gly  Phe  Glu  Lys  Ala  Ala  Ser  Gln  Pro  Gly
115                      120                      125

GAA  CTC  AAG  GAC  TGG  TTT  GTG  GGT  CGA  AGC  AAT  GCC  CAG  GGA  ATA  GAT        848
Glu  Leu  Lys  Asp  Trp  Phe  Val  Gly  Arg  Ser  Asn  Ala  Gln  Gly  Ile  Asp
130                      135                      140                      145

CTG  AAC  CGG  AAC  TTT  CCA  GAC  CTG  GAT  AGG  ATA  GTG  TAC  GTG  AAT  GAG        896
Leu  Asn  Arg  Asn  Phe  Pro  Asp  Leu  Asp  Arg  Ile  Val  Tyr  Val  Asn  Glu
                         150                      155                      160

AAA  GAA  GGT  GGT  CCA  AAT  AAT  CAT  CTG  TTG  AAA  AAT  ATG  AAG  AAA  ATT        944
Lys  Glu  Gly  Gly  Pro  Asn  Asn  His  Leu  Leu  Lys  Asn  Met  Lys  Lys  Ile
               165                      170                      175

GTG  GAT  CAA  AAC  ACA  AAG  CTT  GCT  CCT  GAG  ACC  AAG  GCT  GTC  ATT  CAT        992
Val  Asp  Gln  Asn  Thr  Lys  Leu  Ala  Pro  Glu  Thr  Lys  Ala  Val  Ile  His
          180                      185                      190

TGG  ATT  ATG  GAT  ATT  CCT  TTT  GTG  CTT  TCT  GCC  AAT  CTC  CAT  GGA  GGA       1040
Trp  Ile  Met  Asp  Ile  Pro  Phe  Val  Leu  Ser  Ala  Asn  Leu  His  Gly  Gly
          195                      200                      205

GAC  CTT  GTG  GCC  AAT  TAT  CCA  TAT  GAT  GAG  ACG  CGG  AGT  GGT  AGT  GCT       1088
Asp  Leu  Val  Ala  Asn  Tyr  Pro  Tyr  Asp  Glu  Thr  Arg  Ser  Gly  Ser  Ala
210                      215                      220                      225

CAC  GAA  TAC  AGC  TCC  TCC  CCA  GAT  GAC  GCC  ATT  TTC  CAA  AGC  TTG  GCC       1136
```

|   |   |   |   |   |   |   |   |   |   |   |   |   |   |   |   |   |
|---|---|---|---|---|---|---|---|---|---|---|---|---|---|---|---|---|
| His | Glu | Tyr | Ser | Ser | Ser | Pro | Asp | Asp | Ala | Ile | Phe | Gln | Ser | Leu | Ala | |
|     |     |     |     | 230 |     |     |     | 235 |     |     |     |     |     | 240 |     | |

```
CGG GCA TAC TCT TCT TTC AAC CCG GCC ATG TCT GAC CCC AAT CGG CCA     1184
Arg Ala Tyr Ser Ser Phe Asn Pro Ala Met Ser Asp Pro Asn Arg Pro
            245             250             255

CCA TGT CGC AAG AAT GAT GAT GAC AGC AGC TTT GTA GAT GGA ACC ACC     1232
Pro Cys Arg Lys Asn Asp Asp Asp Ser Ser Phe Val Asp Gly Thr Thr
        260             265             270

AAC GGT GGT GCT TGG TAC AGC GTA CCT GGA GGG ATG CAA GAC TTC AAT     1280
Asn Gly Gly Ala Trp Tyr Ser Val Pro Gly Gly Met Gln Asp Phe Asn
    275             280             285

TAC CTT AGC AGC AAC TGT TTT GAG ATC ACC GTG GAG CTT AGC TGT GAG     1328
Tyr Leu Ser Ser Asn Cys Phe Glu Ile Thr Val Glu Leu Ser Cys Glu
290             295             300             305

AAG TTC CCA CCT GAA GAG ACT CTG AAG ACC TAC TGG GAG GAT AAC AAA     1376
Lys Phe Pro Pro Glu Glu Thr Leu Lys Thr Tyr Trp Glu Asp Asn Lys
                310             315             320

AAC TCC CTC ATT AGC TAC CTT GAG CAG ATA CAC CGA GGA GTT AAA GGA     1424
Asn Ser Leu Ile Ser Tyr Leu Glu Gln Ile His Arg Gly Val Lys Gly
            325             330             335

TTT GTC CGA GAC CTT CAA GGT AAC CCA ATT GCG AAT GCC ACC ATC TCC     1472
Phe Val Arg Asp Leu Gln Gly Asn Pro Ile Ala Asn Ala Thr Ile Ser
        340             345             350

GTG GAA GGA ATA GAC CAC GAT GTT ACA TCC GCA AAG GAT GGT GAT TAC     1520
Val Glu Gly Ile Asp His Asp Val Thr Ser Ala Lys Asp Gly Asp Tyr
355             360             365

TGG AGA TTG CTT ATA CCT GGA AAC TAT AAA CTT ACA GCC TCA GCT CCA     1568
Trp Arg Leu Leu Ile Pro Gly Asn Tyr Lys Leu Thr Ala Ser Ala Pro
370             375             380             385

GGC TAT CTG GCA ATA ACA AAG AAA GTG GCA GTT CCT TAC AGC CCT GCT     1616
Gly Tyr Leu Ala Ile Thr Lys Lys Val Ala Val Pro Tyr Ser Pro Ala
            390             395             400

GCT GGG GTT GAT TTT GAA CTG GAG TCA TTT TCT GAA AGG AAA GAA GAG     1664
Ala Gly Val Asp Phe Glu Leu Glu Ser Phe Ser Glu Arg Lys Glu Glu
        405             410             415

GAG AAG GAA GAA TTG ATG GAA TGG TGG AAA ATG ATG TCA GAA ACT TTA     1712
Glu Lys Glu Glu Leu Met Glu Trp Trp Lys Met Met Ser Glu Thr Leu
    420             425             430

AAT TTT TAAAAGGCT TCTAGTTAGC TGCTTTAAAT CTATCTATAT AATGTAGTAT      1768
Asn Phe
435

GATGTAATGT GGTCTTTTTT TTAGATTTTG TGCAGTTAAT ACTTAACATT GATTTATTTT  1828
TTAATCATTT AAATATTAAT CAACTTTCCT TAAAATAAAT AGCCTCTTAG GTAAAATAT   1888
AAGAACTTGA TATATTTCAT TCTCTTATAT AGTATTCATT TTCCTACCTA TATTACACAA  1948
AAAAGTATAG AAAAGATTTA AGTAATTTTG CCATCCTAGG CTTAAATGCA ATATTCCTGG  2008
TATTATTTAC AATGCAGAAT TTTTGAGTA ATTCTAGCTT TCAAAAATTA GTGAAGTTCT   2068
TTTACTGTAA TTGGTGACAA TGTCACATAA TGAATGCTAT TGAAAGGTT AACAGATACA   2128
GCTCGGAGTT GTGAGCACTC TACTGCAAGA CTTAAATAGT TCAGTATAAA TTGTCGTTTT  2188
TTTCTTGTGC TGACTAACTA TAAGCATGAT CTTGTTAATG CATTTTTGAT GGGAAGAAAA  2248
GGTACATGTT TACAAAGAGG TTTTATGAAA AGAATAAAAA TTGACTTCTT GCTTGTACAT  2308
ATAGGAGCAA TACTATTATA TTATGTAGTC CGTTAACACT ACTTAAAAGT TTAGGGTTTT  2368
CTCTTGGTTG TAGAGTGGCC CAGAATTGCA TTCTGAATGA ATAAAGGTTA AAAAAAAATC  2428
CCCAGTGAAA AAAAA                                                  2443
```

( 2 ) INFORMATION FOR SEQ ID NO:2:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Arg Leu Gln Gln Glu Asp Gly Ile Ser Phe Glu Tyr His Arg Tyr Pro
 1               5                  10                  15

Glu Leu Arg Glu Ala Leu Val Ser Val Trp Leu Gln Cys Thr Ala Ile
            20                  25                  30

Ser Arg Ile Tyr Thr Val Gly Arg Ser Phe Glu Gly Arg Glu Leu Leu
        35                  40                  45

Val Ile Glu Leu Ser Asp Asn Pro Gly Val His Glu Pro Gly Glu Pro
    50                  55                  60

Glu Phe Lys Tyr Ile Gly Asn Met His Gly Asn Glu Ala Val Gly Arg
65                  70                  75                  80

Glu Leu Leu Ile Phe Leu Ala Gln Tyr Leu Cys Asn Glu Tyr Gln Lys
                85                  90                  95

Gly Asn Glu Thr Ile Val Asn Leu Ile His Ser Thr Arg Ile His Ile
            100                 105                 110

Met Pro Ser Leu Asn Pro Asp Gly Phe Glu Lys Ala Ala Ser Gln Pro
        115                 120                 125

Gly Glu Leu Lys Asp Trp Phe Val Gly Arg Ser Asn Ala Gln Gly Ile
    130                 135                 140

Asp Leu Asn Arg Asn Phe Pro Asp Leu Asp Arg Ile Val Tyr Val Asn
145                 150                 155                 160

Glu Lys Glu Gly Gly Pro Asn Asn His Leu Leu Lys Asn Met Lys Lys
                165                 170                 175

Ile Val Asp Gln Asn Thr Lys Leu Ala Pro Glu Thr Lys Ala Val Ile
            180                 185                 190

His Trp Ile Met Asp Ile Pro Phe Val Leu Ser Ala Asn Leu His Gly
        195                 200                 205

Gly Asp Leu Val Ala Asn Tyr Pro Tyr Asp Glu Thr Arg Ser Gly Ser
    210                 215                 220

Ala His Glu Tyr Ser Ser Ser Pro Asp Asp Ala Ile Phe Gln Ser Leu
225                 230                 235                 240

Ala Arg Ala Tyr Ser Ser Phe Asn Pro Ala Met Ser Asp Pro Asn Arg
                245                 250                 255

Pro Pro Cys Arg Lys Asn Asp Asp Ser Ser Phe Val Asp Gly Thr
            260                 265                 270

Thr Asn Gly Gly Ala Trp Tyr Ser Val Pro Gly Gly Met Gln Asp Phe
        275                 280                 285

Asn Tyr Leu Ser Ser Asn Cys Phe Glu Ile Thr Val Glu Leu Ser Cys
    290                 295                 300

Glu Lys Phe Pro Pro Glu Glu Thr Leu Lys Thr Tyr Trp Glu Asp Asn
305                 310                 315                 320

Lys Asn Ser Leu Ile Ser Tyr Leu Glu Gln Ile His Arg Gly Val Lys
                325                 330                 335

Gly Phe Val Arg Asp Leu Gln Gly Asn Pro Ile Ala Asn Ala Thr Ile
            340                 345                 350

Ser Val Glu Gly Ile Asp His Asp Val Thr Ser Ala Lys Asp Gly Asp
        355                 360                 365
```

|     |     |     |     |     |     |     |     |     |     |     |     |     |     |
| --- | --- | --- | --- | --- | --- | --- | --- | --- | --- | --- | --- | --- | --- |
| Tyr | Trp<br>370 | Arg | Leu | Leu | Ile | Pro<br>375 | Gly | Asn | Tyr | Lys | Leu<br>380 | Thr | Ala | Ser | Ala |
| Pro<br>385 | Gly | Tyr | Leu | Ala | Ile | Thr<br>390 | Lys | Lys | Val | Ala<br>395 | Val | Pro | Tyr | Ser | Pro<br>400 |
| Ala | Ala | Gly | Val | Asp<br>405 | Phe | Glu | Leu | Glu | Ser<br>410 | Phe | Ser | Glu | Arg | Lys<br>415 | Glu |
| Glu | Glu | Lys | Glu<br>420 | Glu | Leu | Met | Glu | Trp<br>425 | Trp | Lys | Met | Met | Ser<br>430 | Glu | Thr |
| Leu | Asn | Phe<br>435 |

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

TGTCGCCAGG CTGGTTTGG                                          19

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TAAACAGGCA AGCTCTCTTC C                                   21

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CAGTGCAGCT CGCGGGAC                                           18

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAGCGAATGT TGATGTAGAA TG                                 22

( 2 ) INFORMATION FOR SEQ ID NO:7:

( i ) SEQUENCE CHARACTERISTICS:
        ( A ) LENGTH: 19 base pairs (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:7:

CCTGATGACG CAATTTTCC                                                                    19

(2) INFORMATION FOR SEQ ID NO:8:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:8:

CAGTGCAGCT CGCGGGAC                                                                     18

(2) INFORMATION FOR SEQ ID NO:9:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:9:

TCCAGGTCTG GGAAGTTAC                                                                    19

(2) INFORMATION FOR SEQ ID NO:10:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:10:

AGTACCAGAA AGGCAATGAG                                                                   20

(2) INFORMATION FOR SEQ ID NO:11:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:11:

GGAACAGCTT GCCCCCGAG                                                                    19

(2) INFORMATION FOR SEQ ID NO:12:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

( x i ) SEQUENCE DESCRIPTION: SEQ ID NO:12:

TACCGCTCCG TGTCTCATC                                                                                                              19

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Met  Asp  Ile  Pro  Phe  Val  Leu  Ser  Ala  Asn  Leu  His  Gly  Gly  Asp
 1              5                        10                       15
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Met  Asp  Ile  Pro  Phe  Val  Leu  Ser  Ala  Asn  Leu  His  Gly  Gly  Asp
 1              5                        10                       15
```

( 2 ) INFORMATION FOR SEQ ID NO:15:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Met  Asp  Ile  Pro  Phe  Val  Leu  Ser  Ala  Asn  Leu  His  Gly  Gly  Asp
 1              5                        10                       15
```

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Met  Asp  Ile  Pro  Phe  Val  Leu  Ser  Ala  Asn  Leu  His  Gly  Gly  Asp
 1              5                        10                       15
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Met  Glu  Ile  Pro  Phe  Val  Leu  Ser  Ala  Asn  Leu  His  Gly  Gly  Asp
 1              5                        10                       15
```

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Leu Ser Leu Pro Phe Val Leu Ser Ala Asn Leu His Gly Gly Ser
  1               5                  10                   15
```

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Lys Thr Glu Thr Phe Val Leu Ser Ala Asn Leu His Gly Gly Ala
  1               5                  10                   15
```